United States Patent
Saito

(10) Patent No.: US 9,706,953 B2
(45) Date of Patent: Jul. 18, 2017

(54) ENDOSCOPE SYSTEM, PROCESSOR OF ENDOSCOPE SYSTEM, AND IMAGE PRODUCING METHOD

(75) Inventor: Takaaki Saito, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 223 days.

(21) Appl. No.: 13/277,759

(22) Filed: Oct. 20, 2011

(65) Prior Publication Data

US 2012/0157768 A1    Jun. 21, 2012

(30) Foreign Application Priority Data

Dec. 15, 2010  (JP) .................................. 2010-279464
Aug. 19, 2011  (JP) .................................. 2011-179655

(51) Int. Cl.
*A61B 1/04* (2006.01)
*A61B 1/06* (2006.01)
(Continued)

(52) U.S. Cl.
CPC ...... *A61B 5/14551* (2013.01); *A61B 1/00009* (2013.01); *A61B 1/043* (2013.01); *A61B 1/045* (2013.01); *A61B 1/063* (2013.01); *A61B 1/0638* (2013.01); *A61B 1/0646* (2013.01); *A61B 1/0653* (2013.01); *A61B 5/6852* (2013.01); *G06T 7/0012* (2013.01);
(Continued)

(58) Field of Classification Search
CPC . A61B 1/00009; A61B 1/041; A61B 1/00052; A61B 1/05
USPC ................... 600/101; 348/30, 40, 45, 68–71
See application file for complete search history.

(56) References Cited

U.S. PATENT DOCUMENTS

| | | | |
|---|---|---|---|
| 4,959,710 A | 9/1990 | Uehara et al. | |
| 5,512,940 A * | 4/1996 | Takasugi et al. | 348/71 |

(Continued)

FOREIGN PATENT DOCUMENTS

| JP | 2648494 B2 | 8/1997 |
|---|---|---|
| JP | 3315188 B2 | 8/2002 |
| JP | 2006-192065 A | 7/2006 |

OTHER PUBLICATIONS

European Search Report dated Apr. 18, 2012.
(Continued)

*Primary Examiner* — John P Leubecker
*Assistant Examiner* — Rajaa El Alami
(74) *Attorney, Agent, or Firm* — McGinn IP Law Group, PLLC

(57) ABSTRACT

First illumination light of a first wavelength range, in which light absorption coefficient of blood hemoglobin varies with oxygen saturation thereof, is projected into a test subject body, to capture a first image signal from the first illumination light as reflected from inside the test subject body. Then second illumination light of a second wavelength range different from the first wavelength range is projected into a test subject body, to capture a second image signal from the second illumination light as reflected from inside the test subject body. A subject image of the test subject is produced from the second image signal. Oxygen saturation levels of the test subject are calculated using the first and second image signals. According to the calculated oxygen saturation levels, color properties of the subject image are changed to produce an oxygen saturation image.

16 Claims, 17 Drawing Sheets

(51) Int. Cl.
*A61B 5/1455* (2006.01)
*A61B 1/00* (2006.01)
*A61B 1/045* (2006.01)
*A61B 5/00* (2006.01)
*G06T 7/00* (2017.01)

(52) U.S. Cl.
CPC ............... *G06T 2207/10024* (2013.01); *G06T 2207/10068* (2013.01); *G06T 2207/10152* (2013.01); *G06T 2207/30101* (2013.01)

(56) References Cited

U.S. PATENT DOCUMENTS 6,826,424 B1 * 11/2004 Zeng et al. .................. 600/476
2005/0167621 A1   8/2005 Zeng et al.

OTHER PUBLICATIONS

European Office Action dated May 6, 2014.
European Office Action dated Jan. 15, 2013.
Extended European Search Report dated Mar. 30, 2015.
European Office Action dated Aug. 23, 2016 in European Application No. 14 183 101.6-1666.

* cited by examiner

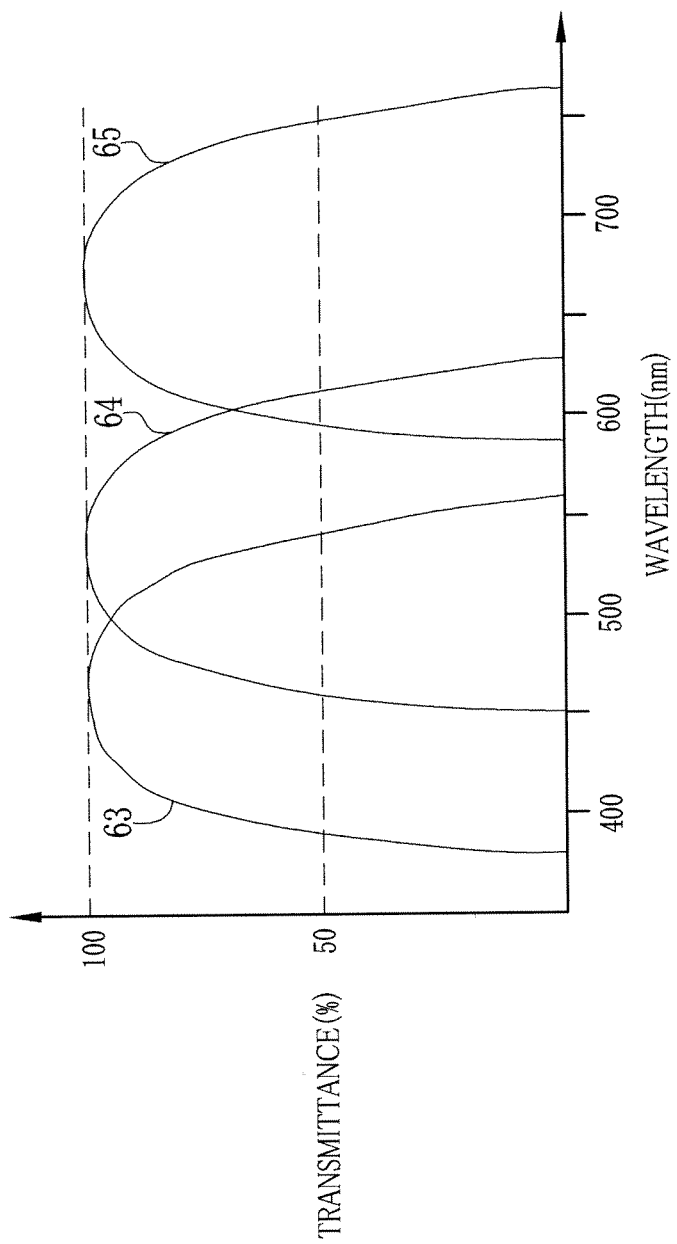

ENDOSCOPE SYSTEM, PROCESSOR OF ENDOSCOPE SYSTEM, AND IMAGE PRODUCING METHOD

BACKGROUND OF THE INVENTION

1. Field of the Invention

The present invention relates to an endoscope system that is adapted to produce an image visualizing information about oxygen saturation of blood hemoglobin. The present invention also relates to a processor and an image producing method for the endoscope system.

2. Description of Related Art

In recent medical field, endoscopes are widely used for diagnoses and treatments. To inspect an interior of a test subject body through the endoscope, white or broadband light is ordinary projected into the test subject body for illumination, but also narrowband light of limited wavelength ranges come to be more frequently used as illumination light for the sake of making particular organs such as blood vessels conspicuous in subsequent endoscopic images displayed on a monitor screen.

Beside the endoscopic inspection using the special narrowband light, it has also been practiced in the art to derive information about vascular functions such as oxygen saturation of blood hemoglobin (percentage of oxygenated hemoglobin in blood vessels) or blood vessel depth from image signals captured by the endoscope, and visualize the derived information in the endoscopic image. For example, Japanese Patent No. 2648494 discloses allocating different colors to different oxygen saturation levels and producing a false-color oxygen saturation image on the basis of the allocated colors.

Japanese Patent No. 3315188 discloses modifying color tones of an endoscopic image according to the oxygen saturation levels, wherein the endoscopic image is captured in a three color frame-sequential fashion using a rotary color filter. Therefore the captured image generally reproduces ordinary colors of the subject. However, a red filter section of the rotary color filter has a wavelength band that is shifted to a range in which light absorbance of oxygenated hemoglobin remarkably differs from that of reduced hemoglobin. Thereby, particularly the hue of red of the endoscopic image will change according to the oxygen saturation level.

The false-color oxygen saturation image suggested in the former-mentioned prior art, however, shows totally different colors from natural or ordinary colors of the living body which is generally tinged with red. As a result, it is difficult to diagnostically inspect changes in mucosal properties. The latter-mentioned prior art, on the other hand, does not have such problem as the former prior art, since only the color tone or the tinge of red of an ordinary color image will change with the change in oxygen saturation. However, because the pixel levels of the red image signal depend not only on the oxygen saturation but also on the blood volume (sum of oxygenated hemoglobin and reduced hemoglobin) in the mucous, it is hard to scale the magnitude of oxygen saturation by the red hue gradation, discriminately from the magnitude of blood volume.

SUMMARY OF THE INVENTION

The present invention has an object to provide an endoscope system that can produce an oxygen saturation image that merges information about oxygen saturation of a subject into an ordinary image of the subject, independently of other biological factors of the subject, especially the blood volume.

The present invention also has an object to provide a processor and an image producing method for that endoscope system.

An endoscope system of the present invention comprises a light projecting device, an image signal capturing device, an image producing device, an oxygen saturation calculating device, and a display device. The light projecting device projects first illumination light of a first wavelength range and second illumination light of a second wavelength range different from the first wavelength range into a test subject body, wherein light absorption coefficient of blood hemoglobin varies with oxygen saturation thereof in the first wavelength range. The image signal capturing device using an imaging device captures a first image signal from the first illumination light as reflected from inside the test subject body and a second image signal from the second illumination light as reflected from inside the test subject body. The image producing device produces a subject image of the test subject from the second image signal, and the oxygen saturation calculating device calculates oxygen saturation levels of the test subject using the first image signal. The oxygen saturation image producing device produces an oxygen saturation image by changing color properties of the subject image according to the calculated oxygen saturation levels, and the display device displays the oxygen saturation image.

The oxygen saturation image producing device may include a color changing amount memory for memorizing oxygen saturation levels in association with color changing amounts served for changing pixel levels of the second image signal according to the oxygen saturation levels, and an image color processing device. The image color processing device determines, with reference to the color changing amount memory, those color changing amounts corresponding to the oxygen saturation levels calculated by the oxygen saturation calculating device, and changes the pixel levels of the second image signal individually by the determined color changing amounts, to produce the oxygen saturation image.

The color changing amounts may have approximately linear relations to the oxygen saturation levels in the color changing amount memory.

The color changing amounts may also be constant regardless of the oxygen saturation levels in a range above a given oxygen saturation level, and increase or decrease depending on the oxygen saturation levels in a range below the given oxygen saturation level. Preferably, the color changing amounts increase or decrease at rates variable gradually according to the oxygen saturation levels.

In an embodiment, the oxygen saturation level given to the color changing amount memory as a threshold to increase or decrease the color changing amounts may be revised in response to information input by a user.

Preferably, the color changing amounts are gains by which pixel levels of the second image signal are multiplied.

In an embodiment, the imaging device may be a color imaging device having red pixels with red color filters, green pixels with green color filters, and blue pixels with blue color filters, outputting red, green and blue signals respectively. In this embodiment, red, green and blue signals as captured under the second illumination light constitute the second image signal, and the oxygen saturation image producing device is configured to lower pixel levels of the red signal among the second image signal with respect to those pixels for which the oxygen saturation levels are calculated to be lower than a given value.

In another embodiment, the light projecting device may project narrowband light as the first illumination light, and blue, green and red rays as the second illumination light, sequentially toward the test subject body. In this embodiment, the imaging device sequentially outputs a narrowband signal captured under the narrowband light as the first image signal, and blue, green and red signals as the second image signal under the blue, green and red rays respectively, and the oxygen saturation image producing device is configured to lower pixel levels of the red signal among the second image signal with respect to those pixels for which the oxygen saturation levels are calculated to be lower than a given value.

The oxygen saturation calculating device preferably extracts information about the oxygen saturation from among various kinds of biological information contained in the first or the second image signal on the basis of the first and second image signals in combination.

The first wavelength range is preferably from 460 nm to 480 nm, and the second wavelength range is preferably from 450 nm to 700 nm.

According to another aspect of the present invention, a processor for an endoscope system comprises a signal receiving device for receiving first and second image signals from an endoscope, an image producing device for producing a subject image of a test subject from the second image signal, an oxygen saturation calculating device for calculating oxygen saturation levels of the test subject using the first image signal, and an oxygen saturation image producing device for producing an oxygen saturation image by changing color properties of the subject image according to the calculated oxygen saturation levels. The endoscope projects first illumination light of a first wavelength range and second illumination light of a second wavelength range different from the first wavelength range into the test subject body, and captures the first image signal and the second image signal respectively from the first illumination light and the second illumination light as reflected from inside the test subject body, wherein light absorption coefficient of blood hemoglobin varies with oxygen saturation thereof in the first wavelength range.

An image producing method of the present invention comprises:

projecting first illumination light of a first wavelength range and second illumination light of a second wavelength range different from the first wavelength range into a test subject body, wherein light absorption coefficient of blood hemoglobin varies with oxygen saturation thereof in the first wavelength range;

capturing a first image signal from the first illumination light as reflected from inside the test subject body;

capturing a second image signal from the second illumination light as reflected from inside the test subject body;

producing a subject image of the test subject from the second image signal;

calculating oxygen saturation levels of the test subject using the first image signal; and producing an oxygen saturation image by changing color properties of the subject image according to the calculated oxygen saturation levels.

According to the present invention, oxygen saturation levels of a test subject are measured based on a first image signal that is captured under first illumination light of a first wavelength range, preferably a narrow blue wavelength range, in which light absorption coefficient of blood hemoglobin varies with oxygen saturation thereof, and an oxygen saturation image is produced by changing color properties of a subject image according to the measured oxygen saturation levels. Since the subject image is produced from a second image signal that is captured under second illumination light of a second wavelength range different from the first wavelength range, the second illumination light being preferably broadband white light, the oxygen saturation image may show information about the measured oxygen saturation levels while reproducing actual condition of the test subject in natural colors in those areas where the oxygen saturation levels are normal. Therefore, the oxygen saturation image obtained in the present invention is superior and useful for medical diagnosis.

Calculating the oxygen saturation levels on the basis of the first and second image signals in combination can extract information about the oxygen saturation independently of other biological factors, such as blood volume.

BRIEF DESCRIPTION OF THE DRAWINGS

The above and other objects and advantages of the present invention will be more apparent from the following detailed description of the preferred embodiments when read in connection to the accompanied drawings, wherein like reference numerals designate like or corresponding parts throughout the several views, and wherein:

FIG. 5 is a graph showing spectral transmittances of RGB color filters;

DESCRIPTION OF THE PREFERRED EMBODIMENTS

Figure 1:
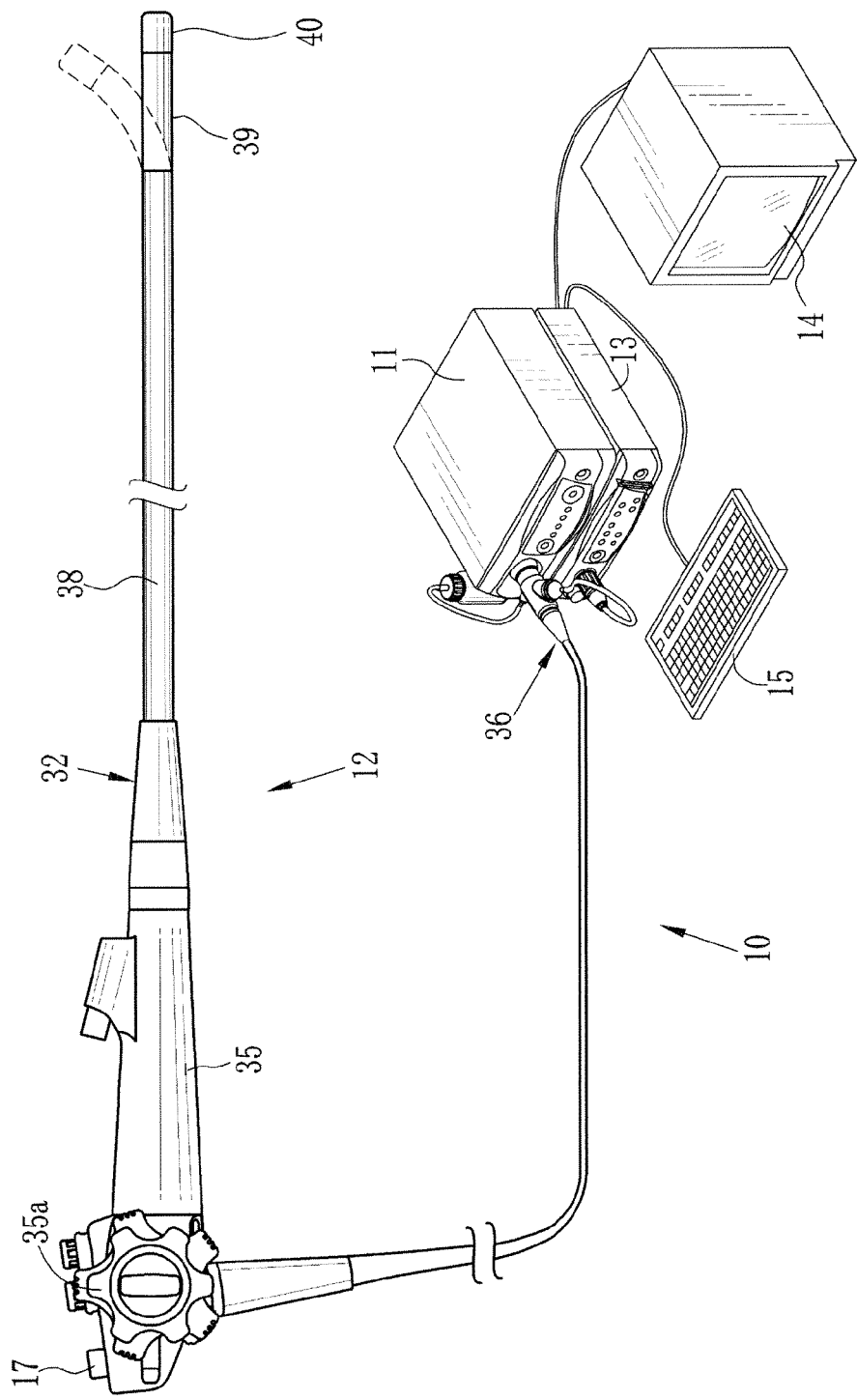
FIG. 1 is a diagram illustrating an outer appearance of an endoscope system according to a first embodiment of the present invention.
Figure 2:
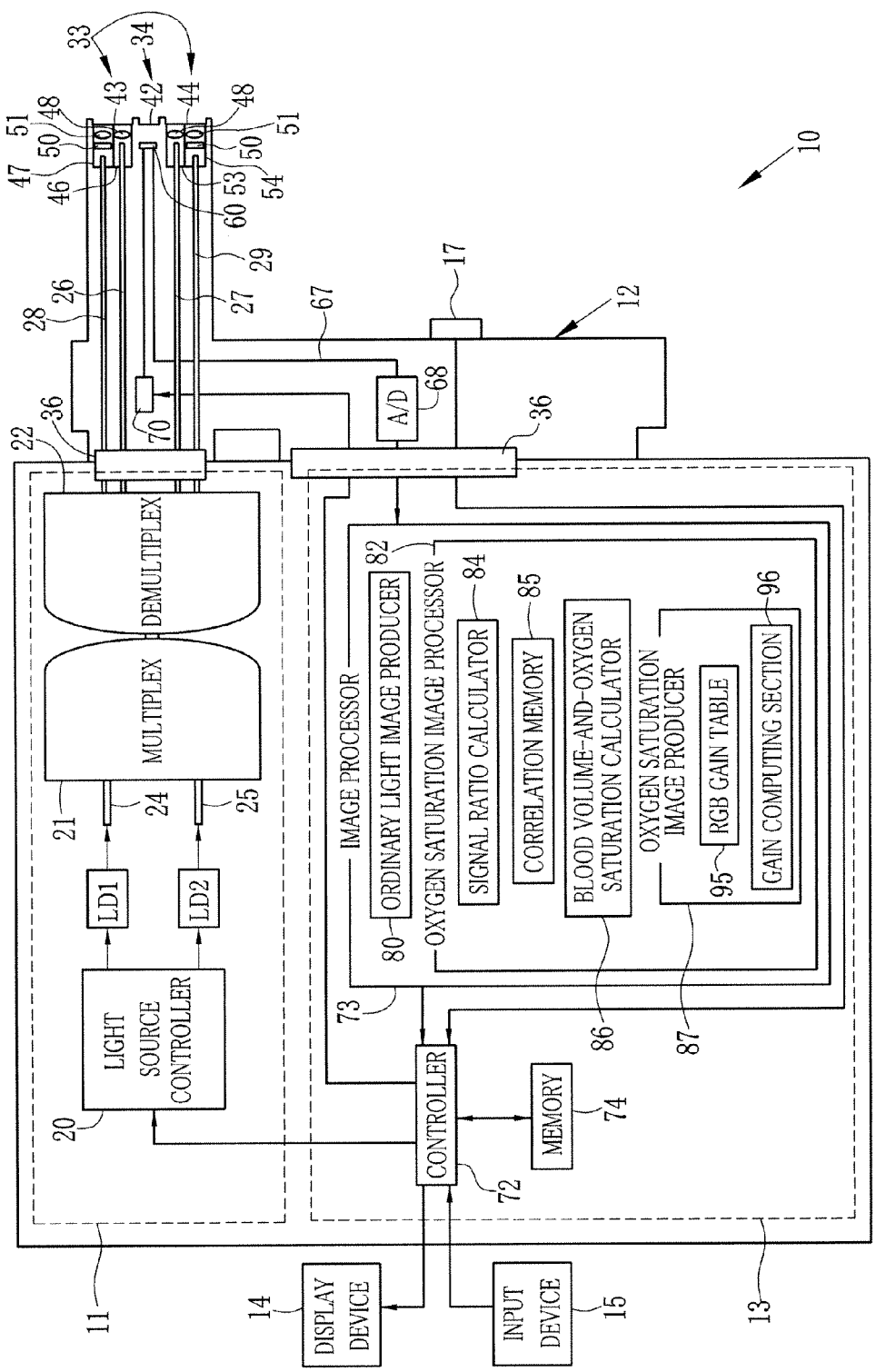
FIG. 2 is a block diagram illustrating an internal structure of the endoscope system of the first embodiment.

As shown in FIGS. 1 and 2, an endoscope system 10 according to the first embodiment of the present invention includes a light source unit 11, an endoscope 12, a processor unit 13, a display device 14, and an input device 15 including a keyboard and the like. The light source unit 11 may emit light of a predetermined wavelength range. The endoscope 12 conducts the light from the light source unit 11 to project it into a target area inside a test subject, and captures images from light reflected from the target area. The processor unit 13 processes image signals captured by the endoscope 12 so that the display device 14 may display an endoscopic image using the processed image signals.

The endoscope system 10 is provided with an ordinary light inspection mode and an oxygen saturation inspection mode. In the ordinary light inspection mode, the display device 14 displays an ordinary light image of the test subject captured under the illumination of visible rays ranging from blue to red wavelength regions. In the oxygen saturation inspection mode, the display device 14 displays an oxygen saturation image, in which information about oxygen saturation of blood hemoglobin of the test subject is reflected on the ordinary light image of the test subject. These inspection modes may be switchable upon instructions entered through a change-over switch 17 of the endoscope 12 or the input device 15.

The light source unit 11 includes two kinds of laser light sources LD1 and LD2, a light source controller 20, a combiner or optical multiplexer 21 and a coupler or optical demultiplexer 22. The laser light source LD1 generates narrow band light for use in measuring oxygen saturation, hereinafter referred to as the oxygen saturation measuring light, which corresponds to the first illumination light in the claims. The laser light source LD2 generates exciting light for exciting a phosphor 50 to emit white light, the phosphor 50 being disposed in a distal end of the endoscope 12. The light beams from the laser light sources LD1 and LD2 are introduced into optical fibers 24 and 25 through not-shown condenser lenses, respectively. Note that the laser light sources LD1 and LD2 may use broad area type InGaN-based laser diodes, InGaNAs-based laser diodes, or GaNAs-based laser diodes.

The light source controller 20 controls the laser light sources LD1 and LD2 to adjust the timing of light emission from the laser light sources LD1 and LD2 as well as the light volume ratio between the laser light sources LD1 and LD2. In the present embodiment, the laser light source LD1 is turned OFF and the laser light source LD2 is turned ON in the ordinary light inspection mode. In the oxygen saturation inspection mode, the laser light sources LD1 and LD2 are alternately turned ON and OFF in the inverted phase at constant intervals.

The combiner 21 combines light beams from the optical fibers 24 and 25. The combined light beams are divided into four beams through the coupler 22 that functions as a branching filter. Among the branched four light beams, ones from the laser light source LD1 are conducted through light guides 26 and 27, and ones from the laser light source LD2 are conducted through light guides 28 and 29. The light guides 26 to 29 may be made of bundle fibers, each consisting of a bundle of many optical fibers. It is alternatively possible to omit the combiner 21 and the coupler 22 and introduce the light beams from the laser light sources LD1 and LD2 directly into the light guides 26 to 29.

The endoscope 12 may be an electronic endoscope having an endoscopic probe 32, a light projecting portion 33, an imaging portion 34, a handling portion 35, and a connector 36 for detachably connecting the endoscope 12 to the light source unit 11 and the processor unit 13. The light projecting portion 33 conducts the light beams through the four light guides 26 to 29 to project them toward a target area, and the imaging portion 34 takes images from the target area through a single imaging device.

The endoscopic portion 32 includes a flexible member 38, a curving member 39, and the scope distal end 40. As the flexible member 38 can bend along the route inside the test body, the endoscopic portion 32 may be smoothly introduced into the test body. Upon rotating an angle knob 35a of the handling portion 35, the curving member 39 may curve in any direction at any angle so that the scope distal end 40 may be oriented to the desired target site inside test body.

Figure 3:
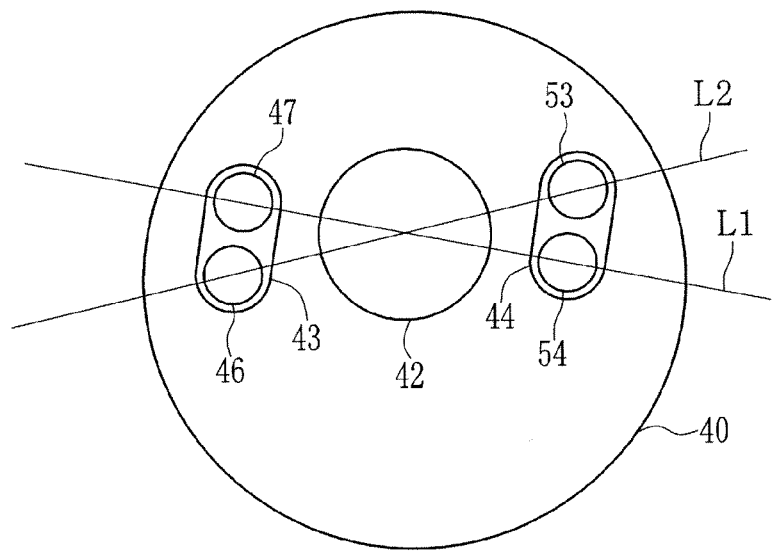
FIG. 3 is a front view of a scope distal end.
Figure 4:
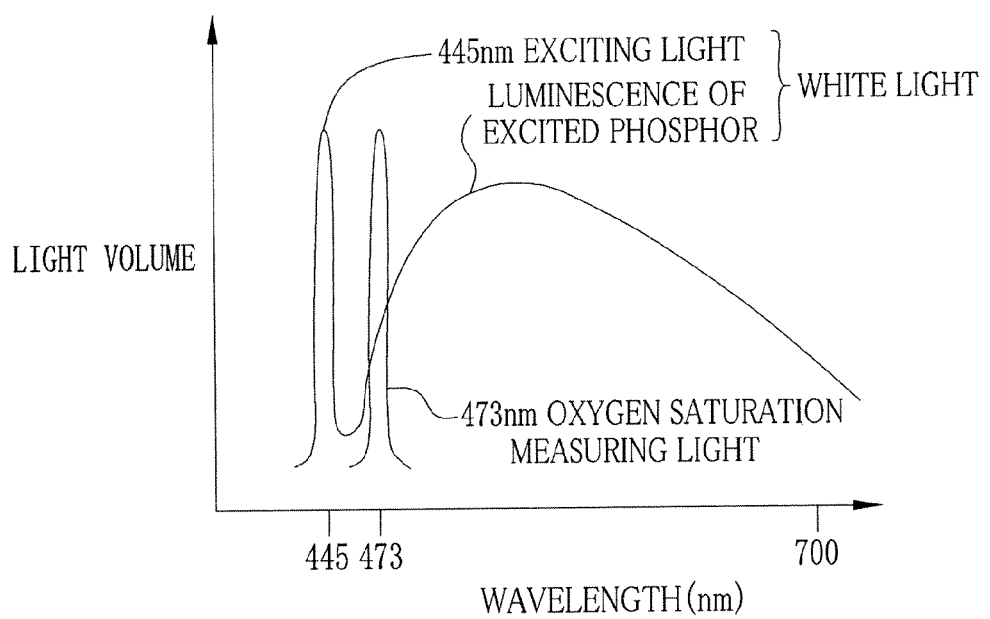
FIG. 4 is a graph showing emission spectra of oxygen saturation measuring light and white light.

The light projecting portion 33 and the imaging portion 34 are provided in the scope distal end 40. The imaging portion 34 has an inspection window 42 in a central position of a front face of the scope distal end 40, and the light projecting portion 33 has two light projecting window 43 and 44 on opposite sides of the inspection window 42, as shown in FIG. 3.

Behind one light projecting window 43 are mounted a couple of light projection units 46 and 47. One light projection unit 46 projects the oxygen saturation measuring light from the light guide 26 through a lens 48 toward the target site or subject area for inspection. In the other light projection unit 47, the exciting light is projected from the light guide 28 onto the phosphor 50, exciting the phosphor 50 to emit white light. Thus, the white light is projected from the light projection unit 47 through a lens 51 toward the target test body site. Behind the other light projecting window 44 are also mounted a couple of light projection units 53 and 54, which have the same structures and functions as the light projection units 46 and 47 respectively.

Through the light projecting windows 43 and 44, the oxygen saturation measuring light or the white light is projected toward the subject area, and light reflected from the subject area is captured by the imaging portion 34 through the inspection window 42.

These four light projection units 46, 47, 53 and 54 are positioned such that a straight line L1 interconnecting outlet surfaces of those light projection units 47 and 54 having the phosphors 50 and a straight line L2 interconnecting outlet surfaces of other two light projection units 46 and 53 having no phosphor 50 intersect at a center of the inspection window 42. Thus the target site may be evenly illuminated.

The phosphor 50 may include various kinds of fluorescent substances, e.g. YAG or BAM ($BaMgAl_{10}O_{17}$) fluorescent substances, which absorb part of the exciting light from the laser light source LD2 to be excited to emit luminescence of green to yellow hues. When the exciting light is projected onto the phosphor 50, the luminescence of green to yellow emitted from the excited phosphor 50, i.e. fluorescence, is mixed with the exciting light that has not been absorbed in the phosphor 50 but transmitted through the phosphor 50, producing the white light or pseudo white light. Note that the phosphor 50 may be one called Micro White (MW) as a trade mark.

Accordingly, the white light projected from the light projection units 47 and 54 having the phosphor 50 each will provide an emission spectrum having a wavelength range around a center wavelength of 445 nm of the exciting light and a wavelength range of about 450 nm to 700 nm where the intensity increases in the fluorescence emitted from the phosphor 50 as excited by the exciting light. On the other hand, the oxygen saturation measuring light from the light projection units 46 and 53 will provide an emission spectrum having a wavelength range around a center wavelength of 473 nm.

It should be noted that the white light in the present disclosure includes not only the white light in the strict meaning, which contain all visible light components, but also any light including the above pseudo white light insofar as it contains rays of specific wavelength bands for the primary colors such as R (red), G (green) and B (blue). That is, the white light in the present disclosure should be broadly interpreted to include light containing wavelength components from green to red and light containing wavelength components from blue to green.

Behind the inspection window 42 are provided optics, including an objective lens unit (not-shown), for obtaining an optical image of the inspection target site of the test body. An imaging device 60, e.g. CCD (charge coupled device) or CMOS (complementary metal-oxide semiconductor), is provided behind the objective lens unit, to capture the optical image of the target site and convert the optical image to an electronic image.

Specifically, the imaging device 60 receives the light from the objective lens unit on a light receiving surface (imaging surface) to convert the received light into analog electric image signal. The imaging device 60 may be a color CCD having many pixel groups arranged in a matrix, wherein each group includes a pixel provided with a red filter (R pixel), a pixel provided with a green filter (G pixel), and a pixel provided with a blue pixel (B pixel).

The color filters for blue, green and red have spectral transmittances 63, 64 and 65, respectively, as shown in FIG. 5. Accordingly, the white light reflected from the inspection site will pass through any of the RGB color filters. Therefore, all of the RGB pixels of the imaging device 60 output the image signal. As for the oxygen saturation measuring light, on the other hand, having the center wavelength of 473 nm, the image signal is mainly output from the B pixels.

The analog image signal output from the imaging device 60 is fed through a scope cable 67 into an A/D converter 68. The A/D converter 68 converts the analog image signal to digital image signal corresponding to voltage levels of the analog image signal. The digital image signal is transferred through the connector 36 to an image processor 73 of the processor unit 13.

Figure 6A:
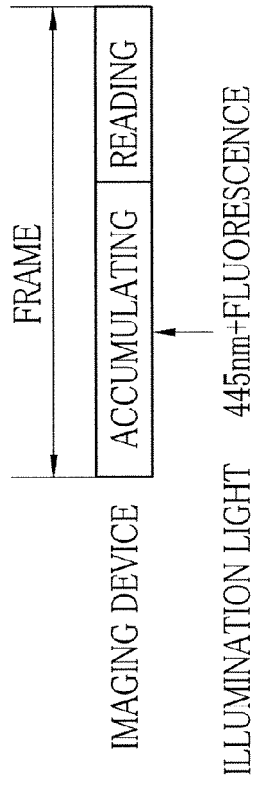
FIG. 6A is an explanatory diagram illustrating an imaging operation of an imaging device in an ordinary light inspection mode.

An imaging controller 70 controls imaging operation of the imaging device 60. In the ordinary light inspection mode, as shown in FIG. 6A, the imaging operation is carried out in two steps within one frame period: accumulating charges acquired through photo-electric conversion of the white light (445 nm+fluorescence), and reading the accumulated charges. These two steps are repeated so long as the system is set at the ordinary light inspection mode. Note that the white light is depicted as being composed of 445 nm ray and fluorescence because the white light is generated by projecting the exciting light of 445 nm onto the phosphor 50.

Figure 6B:
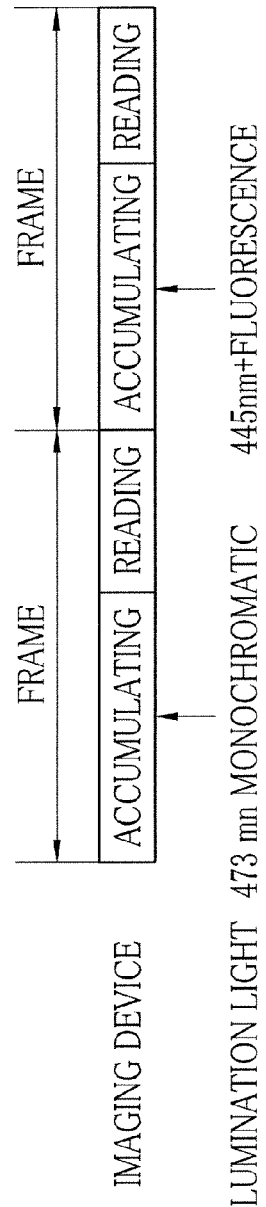
FIG. 6B is an explanatory diagram illustrating an imaging operation of the imaging device in an oxygen saturation inspection mode.

In the oxygen saturation inspection mode, as shown in FIG. 6B, a step of accumulating charges acquired through photo-electric conversion of the oxygen saturation measuring light (narrowband light around 473 nm) and a step of reading the accumulated charges are carried out in one frame period. In the next frame period, a step of accumulating charges acquired through photo-electric conversion of the white light (445 nm+fluorescence or MW), and a step of reading the accumulated charges are carried out. The imaging operation of these two frame periods is carried out cyclically so long as the system is set at the oxygen saturation inspection mode.

In the oxygen saturation inspection mode, the image signal of the first frame consists of blue signal B1 from the B pixels of the imaging device 60, green signal G1 from the G pixels, and red signal R1 from the R pixels, whereas the image signal of the second frame is the same ordinary light image signal as obtained in the ordinary light inspection mode, consisting of blue signal B2 from the B pixels, green signal G2 from the G pixels, and red signal R2 from the R pixels.

Although it is not shown in the drawings, channels are provided along inside the handling portion 35 and the endoscopic probe 32 of the endoscope 12, for inserting medical treatment tools or catheters, for sending gas or water, etc.

The processor unit 13 includes a controller 72, an image processor 73, and a memory 74. The controller 72 is connected to the display device 14 and the input device 15. The controller 72 controls the operations of the image processor 73, the light source controller 20 of the light source unit 11, the imaging controller 70 of the endoscope 12, and the display device 14 on the basis of instructions, such as the mode switching instruction, entered through the change-over switch 17 of the endoscope 12 or the input device 15.

The image processor 73 includes an ordinary light image producer 80 and an oxygen saturation image processor 82, and processes the digital image signal from the endoscope 12 appropriately. The ordinary light image producer 80 processes the ordinary light image signal to produce the ordinary light image.

The oxygen saturation image processor 82 calculates information about blood volume and blood hemoglobin of the test subject on the basis of the image signal acquired by the endoscope 12, and produces an oxygen saturation image that reflects the information about the oxygen saturation is reflected on the ordinary light image. The oxygen saturation image processor 82 includes a signal ratio calculator 84, a correlation memory 85, a blood volume-and-oxygen saturation calculator 86, these components 84, 85 and 86 embody an oxygen saturation calculating device of the claimed invention, and an oxygen saturation image producer 87.

The signal ratio calculator 84 calculates a signal ratio between corresponding pixels of the image signals acquired in the first and second frames in the oxygen saturation inspection mode, the corresponding pixels being located at the same position in either frame. The signal ratio is calculated with respect to every pixel of the image signals. In the present embodiment, the signal ratio calculator 84 calculates a signal ratio B1/G2 of the blue signal B1 of the first frame to the green signal G2 of the second frame, as well as a signal ratio R2/G2 of the red signal R2 of the second frame to the green signal G2 of the second frame. It is to be noted that the signal ratios may be calculated with respect to merely those pixels which represent blood vessels in the image signal. In that case, the pixels representing blood vessels may be discriminated based on differences in image signal level between blood vessels and other parts.

Figure 7:
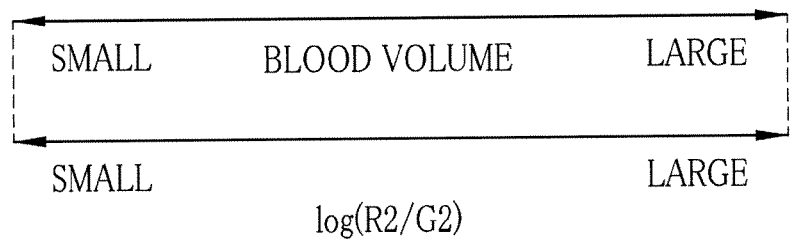
FIG. 7 is a graph showing a correlation between blood volume and a signal ratio R2/G2.

The correlation memory 85 memorizes correlation between the signal ratios B1/G2 and R2/G2 and the blood volume and the oxygen saturation. As shown in FIG. 7, the correlation may be memorized as a linear table defining that the blood volume increases as the signal ratio R2/G2 increases, wherein the signal ratio R2/G2 is memorized to a logarithmic scale.

Figure 8:
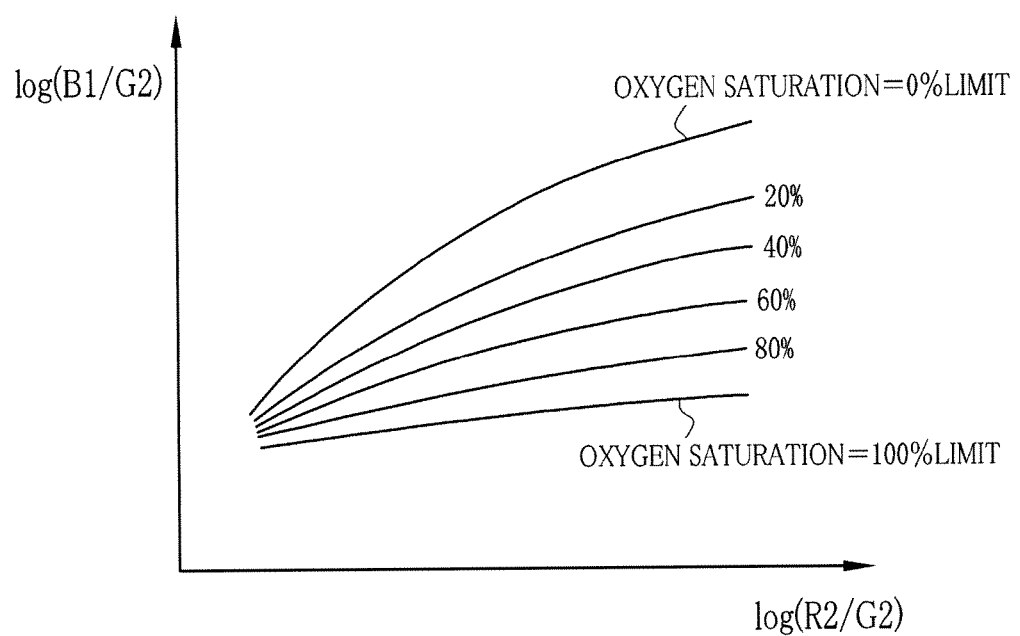
FIG. 8 is a graph showing a correlation between oxygen saturation and signal ratios B1/G2 and R2/G2.

On the other hand, the correlation between the signal ratios and the oxygen saturation is memorized as a two-dimensional table defining level lines of the oxygen saturation in a two-dimensional space, as shown in FIG. 8. The positions and the contour of these level lines may be acquired through physical simulation of light scattering and are defined to vary depending upon the blood volume. For example, the distances between the level lines get wider or narrower with a change in blood volume. Note that the signal ratios B1/G2 and R2/G2 are memorized on the logarithmic scale.

Figure 9:
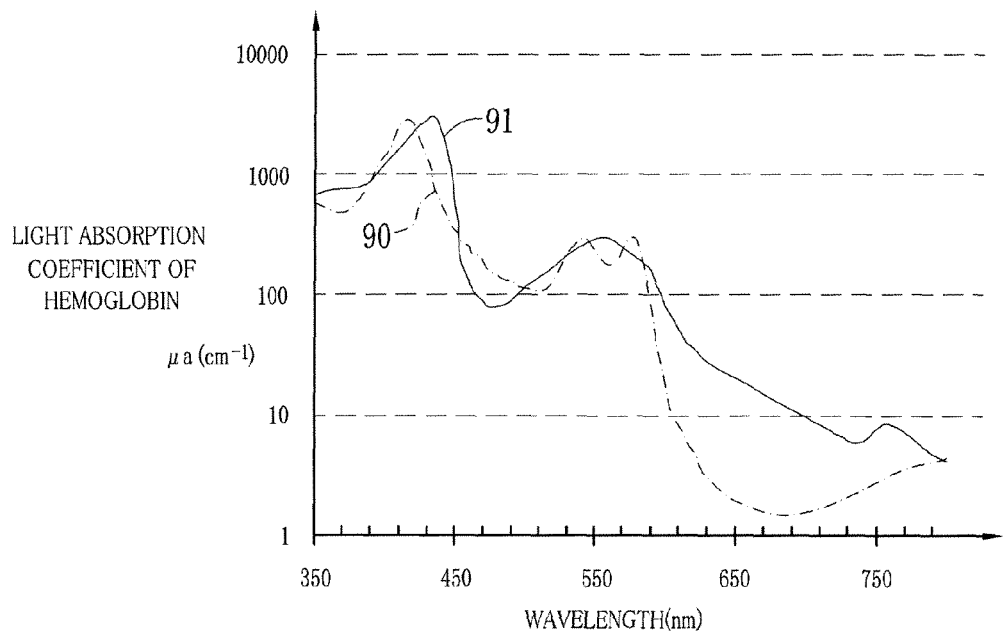
FIG. 9 is a graph showing light absorption coefficient of hemoglobin.

The above correlations closely relate to light absorption characteristics of oxygenated hemoglobin and reduced hemoglobin, as shown in FIG. 9, wherein a curve 90 represents the light absorption coefficient of oxygenated hemoglobin, and a curve 91 represents the light absorption coefficient of oxygenated hemoglobin the light absorption coefficient of reduced hemoglobin. As seen from these curves, information on the oxygen saturation may be acquired more easily at such a wavelength as 473 nm where the light absorption coefficient of oxygenated hemoglobin greatly differs from that of reduced hemoglobin. However, the blue signal containing a signal component corresponding to a ray of 473 nm highly depends on the blood volume as well as the oxygen saturation. Because the red signal R2 corresponds to those rays which will vary mainly depending on the blood volume, and the green signal G2 may be served as a reference signal to the blue signal B1 and the red signal R2, the oxygen saturation can be determined exactly and independently of the blood volume using the signal ratios B1/G2 and R2/G2.

Regarding the dependency of light absorption coefficient of blood hemoglobin on wavelength, the following three aspects may be recited:

The light absorption coefficient varies greatly according to changes in the oxygen saturation in a wavelength range around 470 nm (e.g. in a blue wavelength range having a center wavelength of 470 nm±10 nm);

Averaged in the green wavelength range of 540 nm to 580 nm, the light absorption coefficient is less influenced by the oxygen saturation; and In the red wavelength range of 590 nm to 700 nm, the light absorption coefficient seems to vary greatly depending on the oxygen saturation, but the light absorption coefficient is in a very low level so that the influence of the oxygen saturation is not great.

Figure 10:
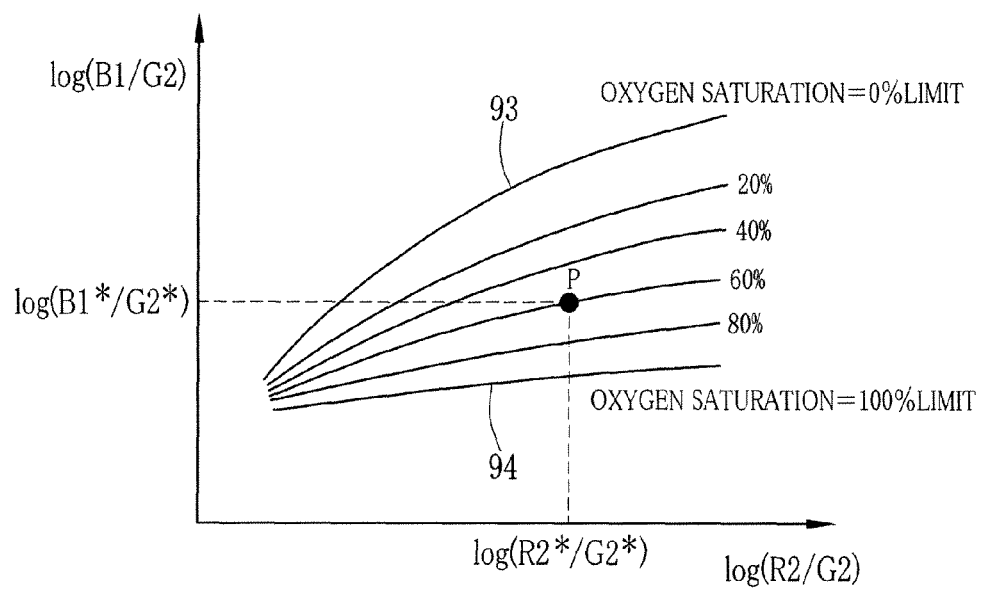
FIG. 10 is an explanatory diagram illustrating a method of deriving oxygen saturation from the signal ratios B1/G2 and R2/G2 based on the correlation shown in FIG. 8.

The blood volume-and-oxygen saturation calculator 86 determines both the blood volume and the oxygen saturation with respect to every pixel of the image signal using the correlation memorized in the correlation memory 85 and the signal ratios B1/G2 and R2/G2 determined by the signal ratio calculator 84. The blood volume will correspond to the signal ratio R2/G2 in the linear table of the correlation memory 85. On the other hand, as for the oxygen saturation, a corresponding point P to particular signal ratios B1*/G2* and R2*/G2* as determined by the signal ratio calculator 84 is determined in the two-dimensional space, as is shown in FIG. 10.

If the corresponding point P is located between a lower-limit line 93 representative of 0% limit of oxygen saturation and an upper-limit line 94 representative of 100% limit of oxygen saturation, the percentage indicated by the level line on which the corresponding point P is located represents the oxygen saturation. In the case illustrated in FIG. 10, for example, the corresponding point P is located on the level line of 60%, the oxygen saturation is 60%. If the corresponding point P is located above the lower-limit line 93, the oxygen saturation is determined to be 0%. If the corresponding point P is located below the upper-limit line 94, the oxygen saturation is determined to be 100%. Alternatively, if the corresponding point P is located above the lower-limit line 93 or below the upper-limit line 94, it may be possible to consider the calculated oxygen saturation unreliable and omit displaying it on the corresponding pixel.

Figure 11:
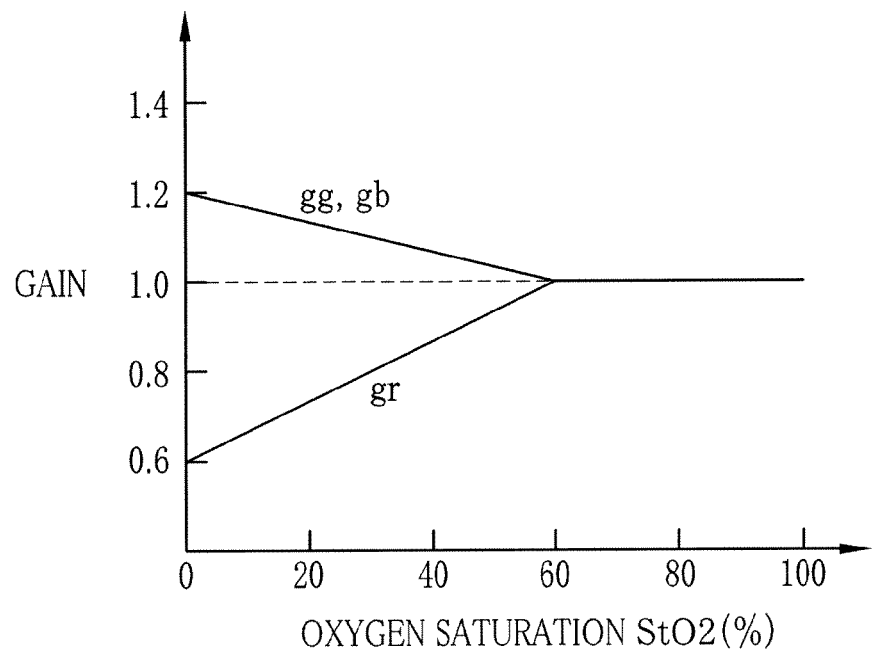
FIG. 11 is a graph showing a relationship between gains and oxygen saturation.

The oxygen saturation image producer 87 includes an RGB gain table 95 corresponding to the claimed color changing amount memory and a gain computing section 96 corresponding to the claimed image color processing device. As shown in FIG. 11, the RGB gain table 95 is configured as a linear LUT (lookup table) defined in a two-dimensional space representing the oxygen saturation along the horizontal axis and respective gains gr, gg and gb to the red, green and blue signals R2, G2 and B2 of the ordinary light image signal along the vertical axis. In the RGB gain table 95, the gains gr, gg and gb are set at "1" in the 100% to 60% oxygen saturation range. In the oxygen saturation range below 60%, the gain gr for the red signal gradually decreases as the oxygen saturation gets lower, whereas the gains gg and gb for the green and blue signals gradually increase as the oxygen saturation gets lower.

The gain computing section 96 incorporates the information on the oxygen saturation into the ordinary light image signal using the blood volume, the oxygen saturation calculated by the blood volume-and-oxygen saturation calculator 86, and the RGB gain table 95. First, the blood volume and the gain corresponding to the oxygen saturation obtained by the gain computing section 96 are determined for each pixel of the ordinary light image signal. Then the determined gain is used to multiply the pixel level of each pixel of the ordinary light image signal, providing an oxygen saturation image that consists of oxygen saturation image signals B2', G2' and R2' as set forth below:

(B2',G2',R2')=(gbB2,ggG2,grR2)

In an alternative, any of color properties of the ordinary light image, such as hue, lightness or color saturation, may be changed according to the oxygen saturation, instead of the pixel levels of the ordinary light image in the present embodiment. In that case, a hue matrix, a lightness matrix or a color saturation matrix, which correlates the oxygen saturation levels with conversion values for converting the hue, the lightness or the color saturation of each pixel of the ordinary light image, shall be used in place of the RGB gain table.

Figure 12:
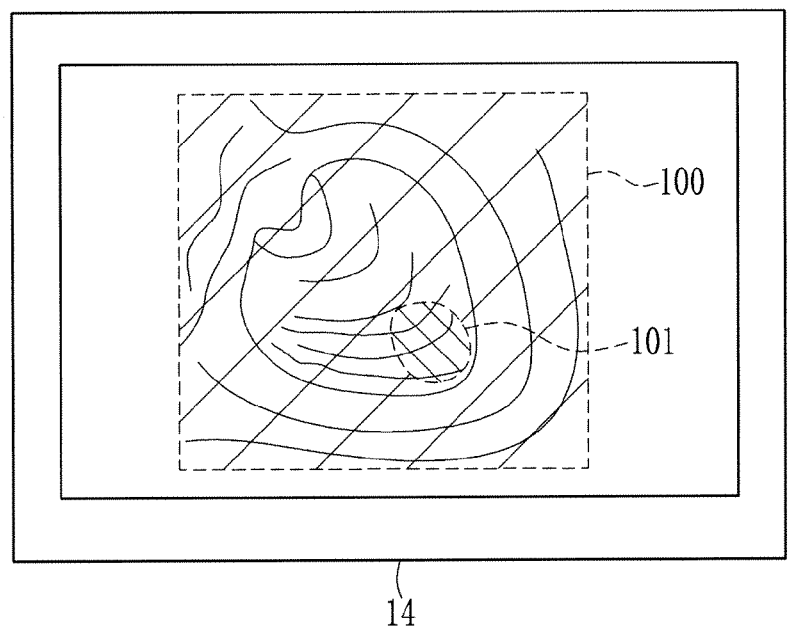
FIG. 12 is a diagram illustrating an example of oxygen saturation images displayed on a screen.

Referring to FIG. 12, since the oxygen saturation image is based on the ordinary light image, a normal area 100 where the oxygen saturation level is normal will be displayed in biologically natural colors. In contrast, an abnormal area 101 where the oxygen saturation level is abnormal will be displayed in an extraordinary color for a living body. The RGB gain table 95 used in the present embodiment is adapted to change the gains higher or lower than "1" for the respective color signals in the oxygen saturation range below 60%. As a result, those pixels of the oxygen saturation image which are in excessively-low oxygen saturation levels, i.e. less than 60%, will increasingly take on the cyan tinge as the oxygen saturation level gets lower. Note that the oxygen saturation is around 70% in normal gastrointestinal mucosa, 100% in arteries, and 70% in veins.

In the present embodiment, the gains for the image signals are changed from "1" in the oxygen saturation range of less than 60%. It is alternatively possible to set the threshold lower than 60% so as to emphasize extremely hypoxic areas alone. It may also be possible to set the threshold higher than 60% in order to emphasize any such areas that are suspected to be hypoxic.

Figure 13:
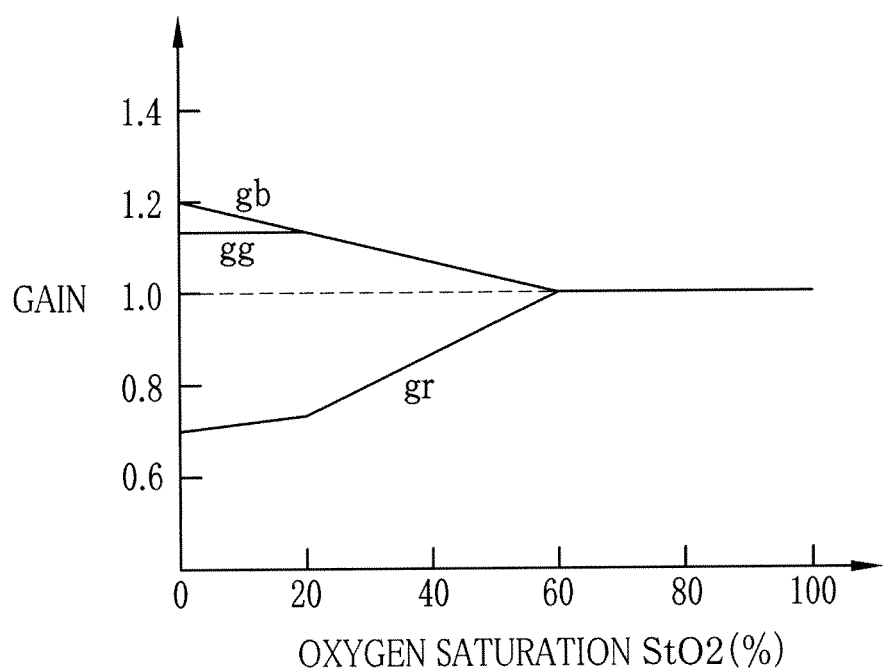
FIG. 13 is a graph showing another relationship between gains and oxygen saturation.

In the RGB table shown in FIG. 11, the gains to the image signals are increased or decreased respectively at constant rates with the decrease of the oxygen saturation from 60%. In an alternative embodiment, the gains may change at variable rates according to the oxygen saturation levels, as shown for example in FIG. 13. According to the RGB gain table of FIG. 13, the gain gr for the red signal decreases at a higher rate in the range of oxygen saturation of 20% to 60% than in the range of oxygen saturation below 20%. On the other hand, the gain gg for the green signal increases at a constant rate in the range of oxygen saturation of 20% to 60%, but is kept substantially unchanged in the range of oxygen saturation below 20%, whereas the gain gb for the blue signal increases at a lower rate in the range of oxygen saturation of 20% to 60% than in the range of oxygen saturation below 20%. Using the RGB gain table of FIG. 13, extremely hypoxic areas where the oxygen saturation is below 20% will get a blue tinge rather than cyan.

Although the color tones are changed by multiplying the respective color pixel levels of the image signal by the determined gains in the above embodiment, offset values corresponding to the determined gains may be added to logarithmically converted image signal instead.

Figure 14:
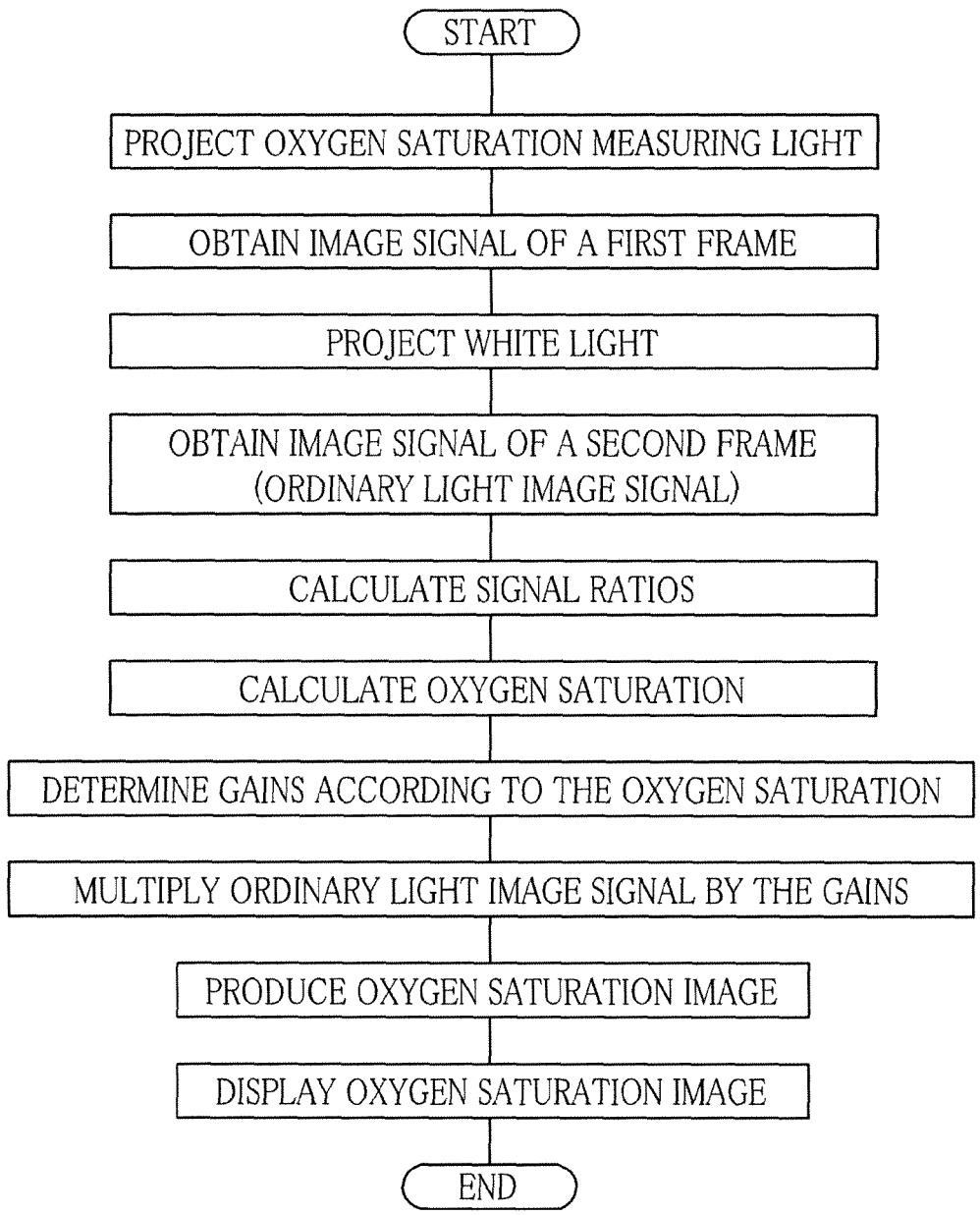
FIG. 14 is a flowchart illustrating the operation of the present invention.
Figure 15:
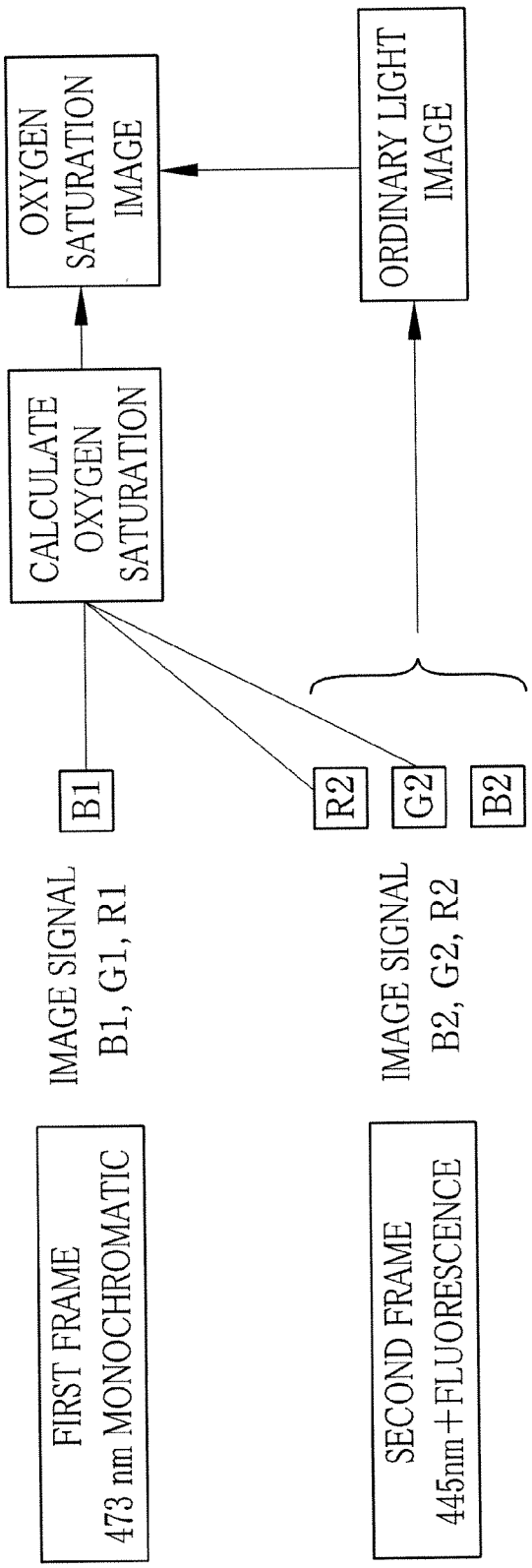
FIG. 15 is a block diagram illustrating a procedure for producing an oxygen saturation image.

Now the operation of the present embodiment will be described with reference to the flowchart of FIG. 14 and the block diagram of FIG. 15. When the system 10 is switched to the oxygen saturation inspection mode by operating the change-over switch 17 of the endoscope 12, the oxygen saturation measuring light or narrowband light of around 473 nm is projected from the endoscope distal end 40 into the test subject body. The oxygen saturation measuring light reflected from the test subject body is received on the imaging device 60, which is a color CCD having B pixels, G pixels and R pixels in the present embodiment, so that image signal, which is composed of blue signal B1, green signal G1, and red signal R1, of a first frame is obtained from the reflected oxygen saturation measuring light.

After the image signal of the first frame is obtained, the white light emitted from the light projecting units 47 and 54 upon the exciting light of around 445 nm is projected from the scope distal end 40 into the test subject body, and the imaging device 60 captures the reflected light from the test subject body, so that image signal, which is composed of blue signal B2, green signal G2, and red signal R2, of the second frame is obtained (namely, an ordinary light image signal corresponding to the second image signal is obtained as recited in the claims).

Then the signal ratio calculator 84 determines the signal ratios B1/G2 and R2/G2 between corresponding pixels of the image signals of the first and second frames located at the same position. These signal ratios are determined with respect to every pixel of the image. Then the blood volume-and-oxygen saturation calculator 86 determines an oxygen saturation level on each pixel corresponding to the signal ratios B1/G2 and R2/G2 determined for each pixel by the signal ratio calculator 84, with reference to the correlation memorized in the correlation memory 85.

When the oxygen saturation levels are determined with respect to all pixels of the image, the gains gb, gg and gr are determined with respect to the individual pixels according to the respective oxygen saturation levels on the basis of the RGB gain table 95. Then the gain computing section 96 multiplies the pixel levels of the blue, green and red signals B2, G2 and R2 of the ordinary light image signal by the determined gains gb, gg and gr, providing blue, green and red signals B2', G2' and R2', respectively. Thus, an oxygen saturation image composed of oxygen saturation image signals composed of the blue, green and red signals B2', G2' and R2' is produced. The oxygen saturation image is displayed on the display device 14.

Figure 16:
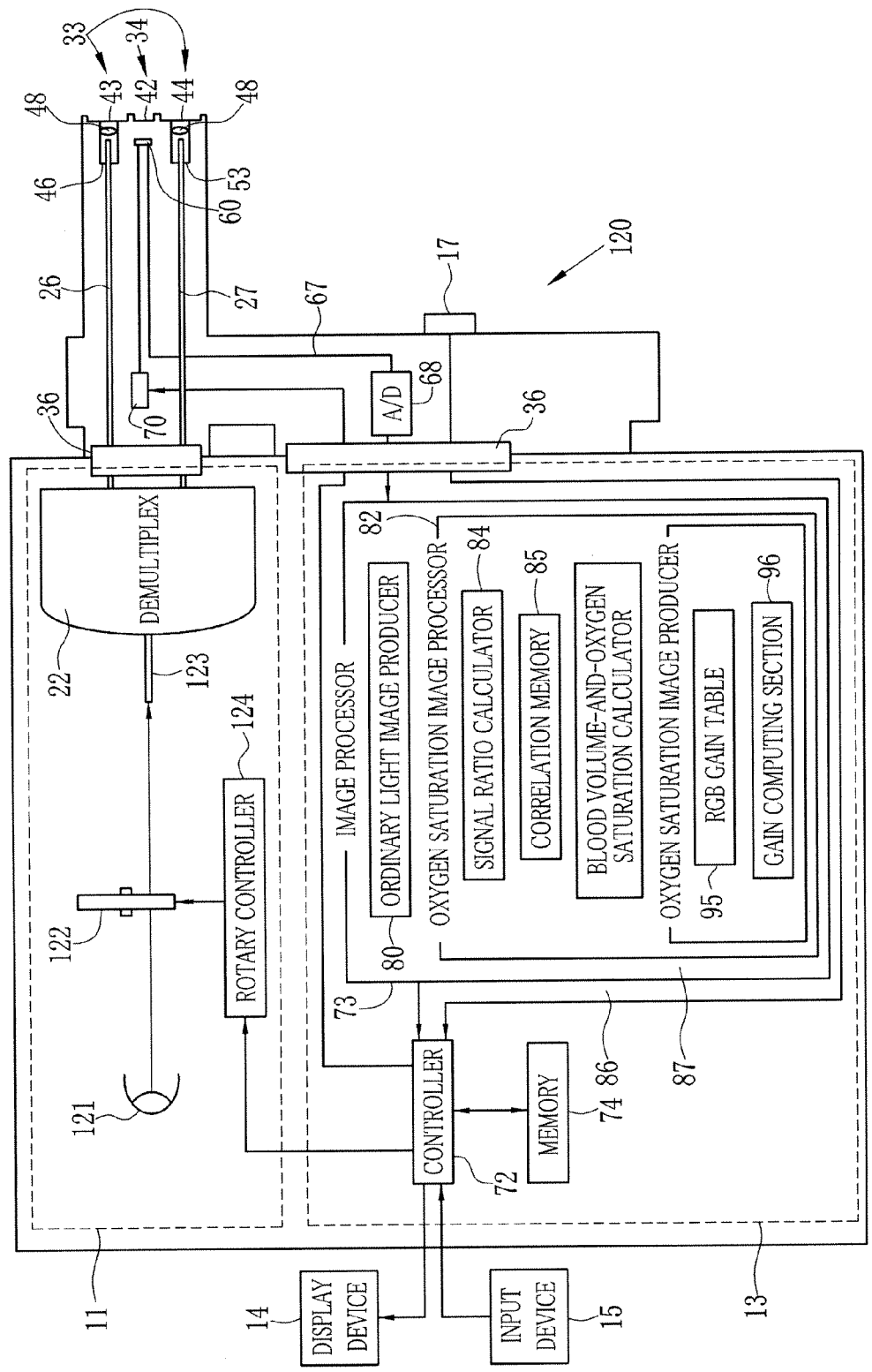
FIG. 16 is a block diagram illustrating an internal structure of an endoscope system according to a second embodiment of the present invention.
Figure 17:
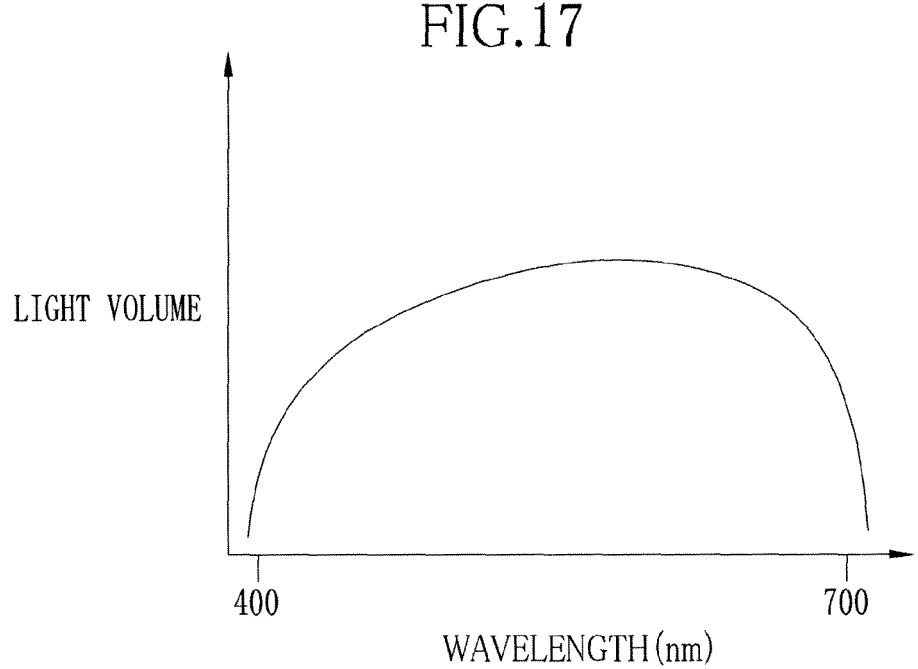
FIG. 17 is a graph illustrating an emission spectrum of white light.

Referring now to FIG. 16, an endoscope system 120 according to a second embodiment of the present invention will be described. The endoscope system 120 adopts a light source unit 11 of a rotary filter type. The rotary filter type light source unit 11 is provided with a broadband light source 121 like a xenon lamp that emits white light having such spectral intensity characteristics as shown in FIG. 17, a rotary filter 122 that transmits either the entire white light or those wavelength components of the white light which correspond to the oxygen saturation measuring light, an optical fiber 123 for receiving and conducting the light transmitted through the rotary filter 122, and a rotary controller 124 for controlling rotation of the rotary filter 122, instead of the laser light sources LD1 and LD2, the light source controller 20 and the combiner 21. The light entering the optical fiber 123 is divided into two beams through a coupler 22. The divided beams are conducted through light guides 26 and 27 and projected from light projection units 46 and 53 into the test subject body, respectively. Other features of the endoscope system 120 may be the same as those of the endoscope system 10, and the description about the same features will be omitted.

Figure 18:
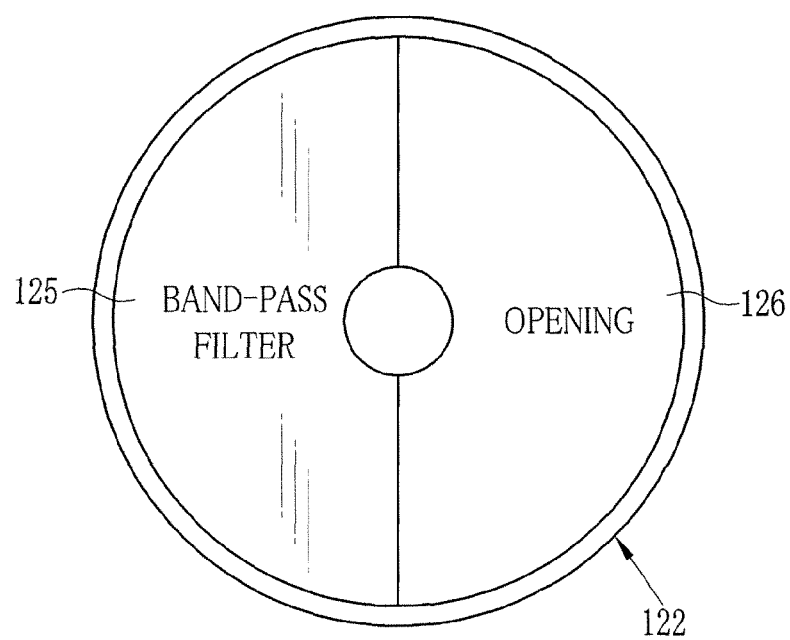
FIG. 18 is a front view of a rotary filter.

As shown in FIG. 18, the rotary filter 122 includes a band-pass filter sector 125 that lets the oxygen saturation measuring light of around 473 nm pass through it among the components of the white light, and an opening 126 for letting the entire white light pass through it. With the rotation of the rotary filter 122, the oxygen saturation measuring light or the white light is alternately projected into the test subject body. Like the first embodiment, image signal of a first frame is obtained when the oxygen saturation measuring light is projected, and image signal of a second frame is obtained when the white light is projected. From the image signals of these first and second frames, an oxygen saturation image is produced in the same way as in the first embodiment. Note that the band-pass filter 125 preferably transmits light components in a wavelength range of 460 nm to 480 nm.

In the second embodiment, as the white light has the spectral intensity characteristics shown in FIG. 17, an ordinary light image signal captured under the white light will contain blue signal B2 corresponding to a wavelength range of 400 nm to 530 nm, green signal G2 corresponding to a wavelength range of 540 nm to 580 nm, and red signal R2 corresponding to a wavelength range of 590 nm to 700 nm.

In the above embodiments, the oxygen saturation level as the threshold for changing the color tone of a particular image area is fixed. In an alternative, the threshold may be shifted by the system user. In that case, a function for shifting the threshold should be added to programs for setting up the endoscope system, in order to modify the RGB gain table on the basis of a threshold value entered through the input device 15.

Among the three color light components of different wavelength ranges, which are served for calculating the blood volume and the oxygen saturation, some may be emitted from semiconductor light source(s) like in the first embodiment, and other may be divided from broadband light BB generated from a white light source like a xenon lamp.

Figure 19:
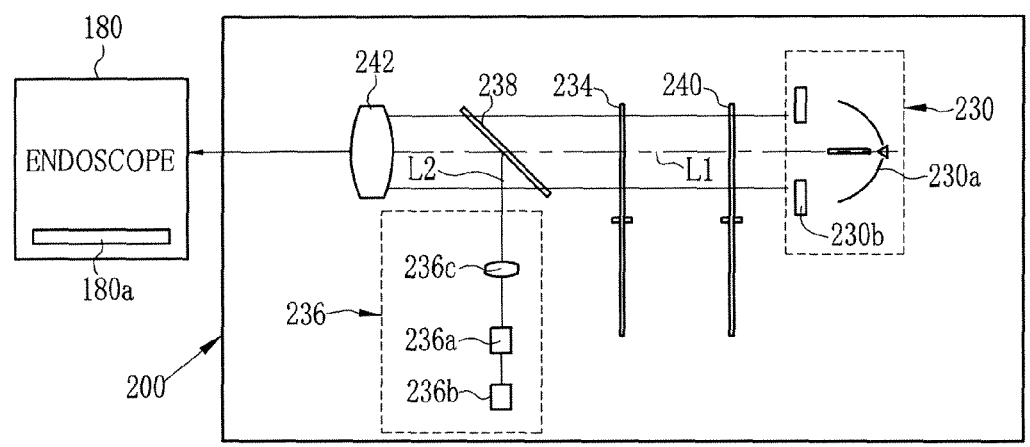
FIG. 19 is a schematic diagram illustrating a light source unit including a semiconductor light source and a white light source.

In that case, a light source unit 200 shown in FIG. 19 may be used instead of the light source unit 11 of the endoscope system 10 of the first embodiment. The light from the light source unit 200 is supplied to an endoscope 180, which has approximately the same structure as the endoscope 12 of the first embodiment, except but a light projecting portion of the endoscope 180 does not include any phosphor. Accordingly, the light from the light source unit 200 is entirely projected into the test subject body via the endoscope 180.

The endoscope 180 should have a different imaging device 180a from the imaging device 60, and an imaging controller should control the imaging device 180a in a different manner from the first embodiment. Moreover, in the embodiment of FIG. 19, an ordinary light image is produced in a different manner from the ordinary light image processor 80 of the processor 12 of the first embodiment, and also an oxygen saturation image is produced using different signals from those used in the oxygen saturation processor 82 of the first embodiment. Essential features of the present embodiment will be described below merely in relation to differences from the first embodiment.

The light source unit 200 includes a white light source 230 that emits a broadband light BB (400 nm to 700 nm), a rotary filter 234 for separating the broadband light BB of the white light source 230 into three color beams of blue, green and red and supplying the respective color beams sequentially to a light guide, a semiconductor light source unit 236 that emits blue narrowband light BN, a light path junction 238 for merging a light path L2 of the blue narrowband light EN into a light path L1 of the broadband light BB, and a shutter blade 240 for blocking the light path L1 of the broadband light BB at predetermined timings between the white light source 230 and the rotary filter 234.

The white light source 230 includes a light source main body 230a radiating the broadband light BB, and a stop member 230b for adjusting light volume of the broadband light BB. The light source main body 230a may include a xenon lamp, a halogen lamp, or a metal halide. The aperture size of the stop member 230b is adjusted by a not-shown light volume controller.

Figure 20:
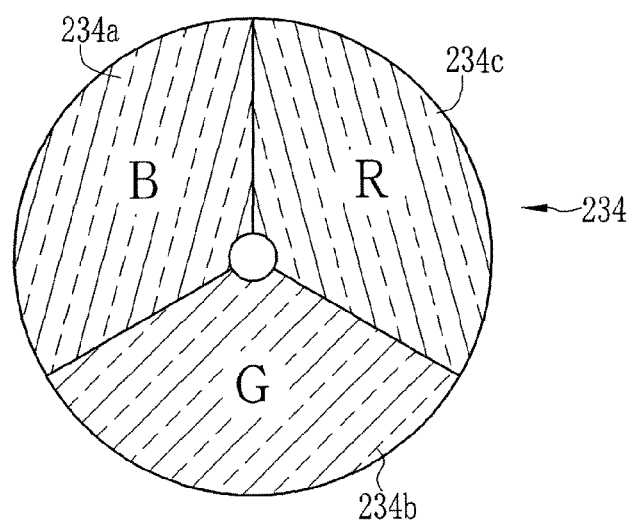
FIG. 20 is a front view of a rotary filter of the light source unit of FIG. 19, subdivided into BGR filter sectors.

As shown in FIG. 20, the rotary filter 234 is shaped into a round disc, which is subdivided into three sectors having a center angle of 120 degrees each, and a blue (B) filter, a green (G) filter and a red (R) filter are provided in these sectors 234a, 234b and 234c, respectively. The rotary filter 234 is mounted rotatable about its center axis such that the B filter sector 234a, the G filter sector 234b and the R filter sector 234c may be selectively inserted into the light path L1 of the broadband light BB.

Figure 21:
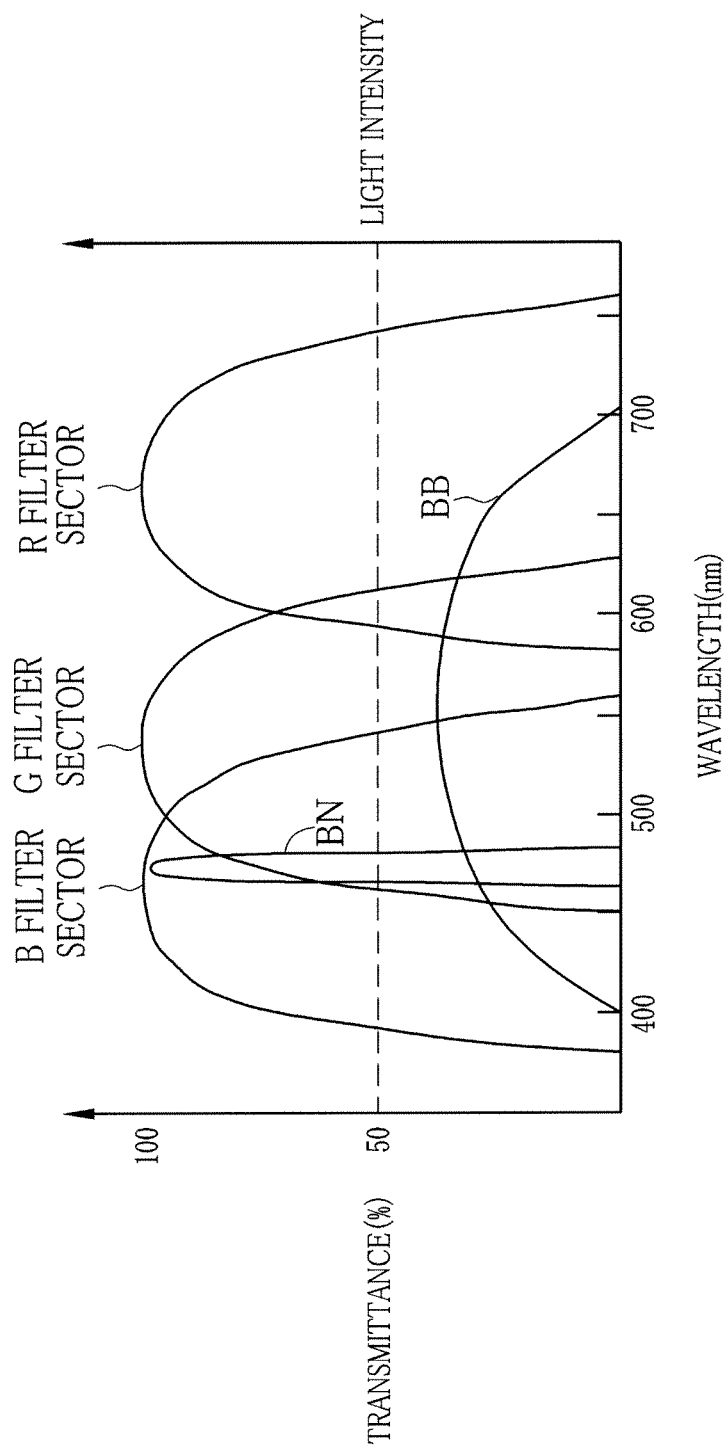
FIG. 21 is a graph showing respective spectral transmittances of the BGR filter sectors and a light intensity curve of blue narrowband light BN.

As shown in FIG. 21, among the components of the broadband light BB, the B filter sector 234a transmits only light components of a blue wavelength band (blue rays), the G filter sector 234b transmits only light components of a green wavelength band (green rays), and the R filter sector 234c transmits only light component of a red wavelength band (red rays). Thus, the blue, green and red rays are sequentially output from the rotating rotary filter 234.

The semiconductor light source unit 236 has a laser light source 236a and a light source controller 236b. As shown in FIG. 21, the laser light source 236a emits the blue narrowband light BN of around 473 nm. The laser light source 236a is turned ON and OFF under the control of the light source controller 236b. The light source controller 236b is controlled by a controller built in the processor unit. The blue narrowband light BN from the laser light source 236a is projected through a condenser lens 236c toward the light path junction 238.

The light path junction 238 may be a dichroic mirror, which entirely transmits the light from the rotary filter 234, but reflects the blue narrowband light BN from the semiconductor light source unit 236 so as to bring the light path L2 of the blue narrowband light BN in line with the light path L1 of the broadband light BB. The light from the light path junction 238 is supplied through a condenser lens 242 to the endoscope 180.

Figure 22:
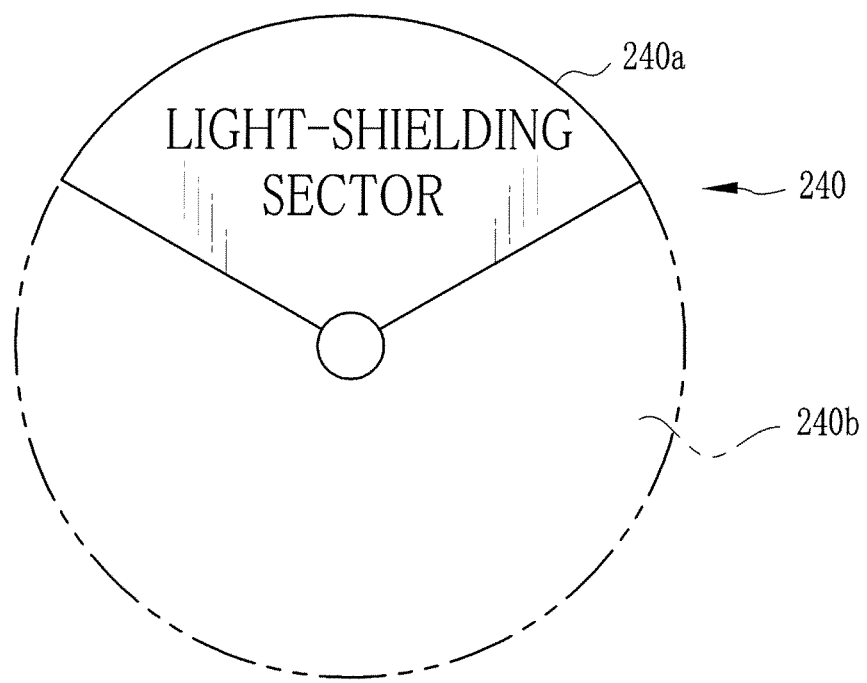
FIG. 22 is a front view of a shutter blade of the light source unit.

As shown in FIG. 22, the shutter blade 240 has a blocking sector 240a at a center angle of 120 degrees for blocking the broadband light BB, and a remaining transparent sector 240b at a center angle of 240 degrees for transmitting the broadband light BB. The shutter blade 240 is rotatable so that the blocking sector 240a or the transparent sector 240b may be alternatively inserted into the light path L1 of the broadband light BB.

The shutter blade 240 is rotated differently between the ordinary light inspection mode and the oxygen saturation inspection mode. In the ordinary light inspection mode, the shutter blade 240 stops at a position where the blocking sector 240a is set out of the light path L1 of the broadband light BB, and the transparent sector 240b is inserted in the light path L1 of the broadband light BB. Therefore the broadband light BB continuously enters the rotary filter 234. According to which of the BGR filter sectors 234a, 234b and 234c is inserted in the light path L1 of the broadband light BB, the blue, the green or the red rays are sequentially produced.

In the oxygen saturation inspection mode, on the other hand, the blocking sector 240a of the shutter blade 240 is inserted in the light path L1 of the broadband light BE, to block the broadband light BB for a predetermined time, while the laser light source 236a is turned ON to supply the blue narrowband light EN to the endoscope 180. When the predetermined time is over, the laser light source 236a is turned OFF and, thereafter, the blocking sector 240a is retracted from the light path L1 of the broadband light BB. Thus the broadband light BB travels sequentially through the B filter sector 234a, the G filter sector 234b and the R filter sector 234c of the rotary filter 234, producing the blue, green and red rays in a sequential fashion.

Unlike the imaging device 60 of the first embodiment, the imaging device 180a of the endoscope 180 is a monochrome imaging device having no micro color filters on its imaging surface. Accordingly, the imaging controller for this imaging device 180a operates in a different manner from the imaging controller 70 of the first embodiment.

Figure 23A:
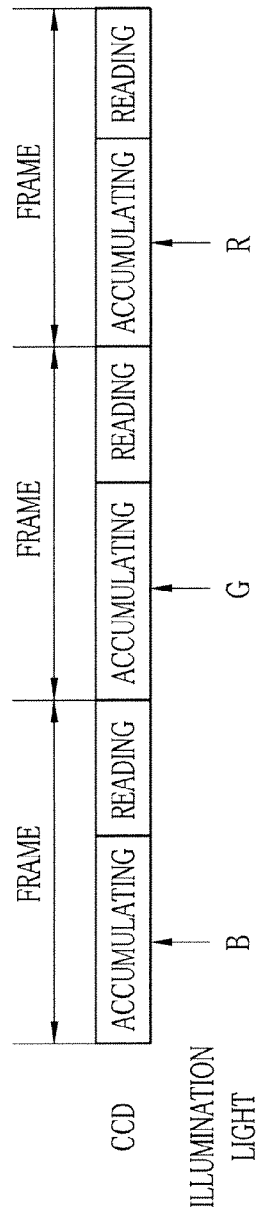
FIG. 23A is an explanatory diagram illustrating an imaging operation of an imaging device in an ordinary light inspection mode using the light source unit of FIG. 19.
Figure 23B:
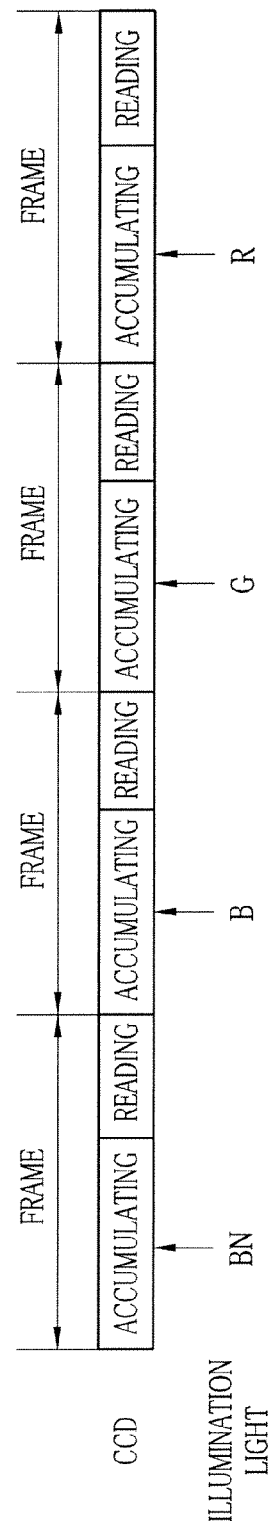
FIG. 23B is an explanatory diagram illustrating an imaging operation of the imaging device in an oxygen saturation inspection mode using the light source unit of FIG. 19.

In the ordinary light inspection mode, as shown in FIG. 23A, the imaging device 180a sequentially receives optical images under the blue, green and red rays, to accumulate charges and output corresponding RGB image signals based on the accumulated charges in a frame-sequential fashion. This operation sequence is cyclically repeated in the ordinary light inspection mode. In the oxygen saturation inspection mode, as shown in FIG. 23B, the imaging device 180a sequentially receives optical images under the blue narrowband light BN, the blue, green and red rays, to accumulate charges and output corresponding frame-sequential image signals for the blue narrowband light BN and the blue, green and red rays, the based on the accumulated charges. This operation sequence is repeated in the oxygen saturation inspection mode.

In the endoscope system using the light source unit 200, the ordinary light image processor of the processor unit produces an ordinary light image based on the frame-sequential three color image signals B, G and R, wherein the frame-sequential blue image signal B substantially corresponds to the blue signal B2 of the first embodiment, the frame-sequential green image signal G substantially corresponds to the green signal G2 of the first embodiment, and the frame-sequential red image signal R substantially corresponds to the red signal R2 of the first embodiment.

Unlike the first embodiment, the oxygen saturation image processor of the second embodiment calculates the blood volume and the oxygen saturation on the basis of the frame-sequential image signals N, G and R. That is, a luminance ratio N/G is used as an element corresponding to the signal ratio B1/G2 of the first embodiment, and a luminance ratio R/G is used as an element corresponding to the signal ratio R2/G2 of the first embodiment. Correspondingly, a correlation memory of the second embodiment memorizes correlation between the luminance ratios N/G and R/G, the blood volume, and the oxygen saturation. Other than the above mentioned, the second embodiment executes the same processes as in the first embodiment.

Although the oxygen saturation levels in the inspected body site are indicated by modifying color properties of an ordinary light image captured under a broadband light in the above embodiments, information about the oxygen saturation may be reflected on an narrowband image (NBI) captured under a narrowband light of a specific wavelength, or on a fluorescent image produced using intrinsic fluorescence or fluorescent agents.

In the above embodiment, oxygen saturation is adopted as information about a biological function of the test subject, to be reflected on the captured endoscopic image. In place of or in addition to the oxygen saturation, oxygenated hemoglobin index determined by multiplying blood volume (sum of oxygenated hemoglobin and reduced hemoglobin) by oxygen saturation (%), or reduced hemoglobin index determined by multiplying blood volume by (100−oxygen saturation (%)) may be used as the information to be reflected on the endoscopic image.

It should be understood that the present invention is not to be limited to the above embodiments, but many variations and modifications of the present invention will be possible for those skilled in the art without departing from the scope of the present invention as specified in the appended claims.

What is claimed is:

1. An endoscope system comprising:
a light projecting device for projecting a first illumination light of a first wavelength range and a second illumination light of a second wavelength range different from the first wavelength range into a test subject body, wherein a light absorption coefficient of blood hemoglobin varies with an oxygen saturation thereof in the first wavelength range;
an image signal capturing device using an imaging device to capture a first image signal from the first illumination light as reflected from inside the test subject body and a second image signal from the second illumination light as reflected from inside the test subject body;
an image producing device for producing a subject image of the test subject from the second image signal;
an oxygen saturation calculating device for numerically calculating oxygen saturation levels of the test subject using the first image signal;
a gain memory for memorizing oxygen saturation levels in association with gains for changing pixel levels of the subject image according to the oxygen saturation levels;
an image color processing device that determines, with reference to said gain memory, the gains corresponding to the oxygen saturation levels calculated by said oxygen saturation calculating device, and the pixel levels of the second image signal being multiplied by the determined gains to produce an oxygen saturation image by changing color properties of the subject image according to the calculated oxygen saturation levels; and
a display device for displaying the oxygen saturation image,
wherein the second illumination light comprises white light, and the subject image comprises an ordinary image captured under the white light,
wherein the gains are constant regardless of the oxygen saturation levels in a range above a given oxygen saturation level in the ordinary light image, and
wherein the gains increase or decrease depending on the oxygen saturation levels in a range below the given oxygen saturation level in the ordinary light image.

2. The endoscope system as recited in claim 1, wherein the gains have approximately linear relations to the oxygen saturation levels in said gain memory.

3. The endoscope system as recited in claim 1, wherein the gains increase or decrease at rates variable gradually according to the oxygen saturation levels.

4. The endoscope system as recited in claim 1, wherein the oxygen saturation level given to said gain memory as a threshold to increase or decrease the gains are revised in response to information input by a user.

5. The endoscope system as recited in claim 2, wherein said imaging device comprises a color imaging device having red pixels with red color filters, green pixels with green color filters, and blue pixels with blue color filters, outputting red, green and blue signals respectively;
red, green and blue signals as captured under the second illumination light constitute the second image signal; and
said oxygen saturation image producing device is configured to lower pixel levels of the red signal among the second image signal with respect to those pixels for which the oxygen saturation levels are calculated to be lower than a given value.

6. The endoscope system as recited in claim 1, wherein said light projecting device projects narrowband light as the first illumination light, and blue, green and red rays as the second illumination light, sequentially toward the test subject body;

said imaging device sequentially outputs a narrowband signal captured under the narrowband light as the first image signal, and blue, green and red signals as the second image signal under the blue, green and red rays respectively; and said oxygen saturation image producing device is configured to lower pixel levels of the red signal among the second image signal with respect to those pixels for which the oxygen saturation levels are calculated to be lower than a given value.

7. The endoscope system as recited in claim 1, wherein said oxygen saturation calculating device extracts information about the oxygen saturation from among various kinds of biological information contained in the first or the second image signal on the basis of the first and second image signals in combination.

8. The endoscope system as recited in claim 1, wherein the first wavelength range is from 460 nm to 480 nm, and the second wavelength range is from 450 nm to 700 nm.

9. The endoscope system as recited in claim 1,
wherein said imaging device comprises a color imaging device having red pixels with red color filters, green pixels with green color filters, and blue pixels with blue color filters, outputting red, green and blue signals respectively,
wherein a first red signal (R1), a first green signal (G1), and a first blue signal (B1) are output as the first image signal from said color imaging device at the time of projecting the first illumination light, and a second red signal (R2), a second green signal (G2), and a second blue signal (B2) are output as the second image signal from said color imaging device at the time of projecting the second illumination light, and
wherein said oxygen saturation calculating device calculates the oxygen saturation levels on the basis of the first blue signal (B1), the second green signal (G2), and the second red signal (R2) in combination.

10. The endoscope system as recited in claim 9, wherein the oxygen saturation calculation device calculates a signal ratio between corresponding pixels of the image signals.

11. The endoscope system as recited in claim 9,
wherein the oxygen saturation calculation device calculates a signal ratio of the first blue signal (B1) to the second green signal (G2) and a signal ratio of the second red signal (R2) to the second green signal (G2).

12. The endoscope system as recited in claim 9,
wherein the oxygen saturation calculating device calculates a signal ratio B1/G2 of the first blue signal (B1) to the second green signal (G2) and a signal ratio R2/G2 of the second red signal (R2) to the second green signal (G2), and
wherein oxygen saturation corresponding to the calculated B1/G2 and R2/G2 is calculated, with reference to correlation between B1/G2, R2/G2 and said oxygen saturation.

13. The endoscope system as recited in claim 1,
wherein said light projecting device projects narrowband light as the first illumination light, and blue, green and red rays as the second illumination light, sequentially toward the test subject body,
wherein said imaging device sequentially outputs a narrowband signal (N) captured under the narrowband light as the first image signal, and a blue signal (B), a green signal (G), and a red signal (R) captured under the blue, green and red rays respectively as the second image signal, and wherein said oxygen saturation calculating device calculates the oxygen saturation levels on the basis of the narrowband signal N, the green signal G, and the red signal R in combination.

14. The endoscope system as recited in claim 1, wherein offset values corresponding to the gains are added to the second image signal.

15. A processor for an endoscope system including an endoscope that projects a first illumination light of a first wavelength range and a second illumination light of a second wavelength range different from the first wavelength range into a test subject body, and captures a first image signal and a second image signal respectively from the first illumination light and the second illumination light as reflected from inside the test subject body, wherein a light absorption coefficient of blood hemoglobin varies with oxygen saturation thereof in the first wavelength range, said processor comprising:

a signal receiving device for receiving the first and second image signals from said endoscope;
an image producing device for producing a subject image of the test subject from the second image signal;
an oxygen saturation calculating device for numerically calculating oxygen saturation levels of the test subject using the first image signal; and
a gain memory for memorizing oxygen saturation levels in association with gains for changing pixel levels of the subject image according to the oxygen saturation levels; and
an image color processing device that determines, with reference to said gain memory, the gains corresponding to the oxygen saturation levels calculated by said oxygen saturation calculating device, and the pixel levels of the second image signal being multiplied by the determined gains to produce an oxygen saturation image by changing color properties of the subject image according to the calculated oxygen saturation levels,
wherein the second illumination light comprises white light, and the subject image comprises an ordinary image captured under the white light,
wherein the gains are constant regardless of the oxygen saturation levels in a range above a given oxygen saturation level in the ordinary light image, and
wherein the gains increase or decrease depending on the oxygen saturation levels in a range below the given oxygen saturation level in the ordinary light image.

16. An image producing method comprising:
projecting a first illumination light of a first wavelength range and a second illumination light of a second wavelength range different from the first wavelength range into a test subject body, wherein a light absorption coefficient of blood hemoglobin varies with oxygen saturation thereof in the first wavelength range;
capturing a first image signal from the first illumination light as reflected from inside the test subject body;
capturing a second image signal from the second illumination light as reflected from inside the test subject body;
producing a subject image of the test subject from the second image signal;
numerically calculating oxygen saturation levels of the test subject using the first image signal; and
memorizing oxygen saturation levels in association with gains for changing pixel levels of the subject image according to the oxygen saturation levels;

determining, with reference to said gains memory, the gains corresponding to the oxygen saturation levels calculated by said oxygen saturation calculating device, and the pixel levels of the second image signal being multiplied by the determined gains to produce an oxygen saturation image by changing color properties of the subject image according to the calculated oxygen saturation levels, wherein the second illumination light comprises white light, and the subject image comprises an ordinary image captured under the white light, wherein the gains are constant regardless of the oxygen saturation levels in a range above a given oxygen saturation level in the ordinary light image, and wherein the gains color increase or decrease depending on the oxygen saturation levels in a range below the given oxygen saturation level in the ordinary light image.

* * * * *